United States Patent
Wise et al.

(10) Patent No.: US 6,838,640 B2
(45) Date of Patent: Jan. 4, 2005

(54) SEPARATION MICROCOLUMN ASSEMBLY FOR A MICROGAS CHROMATOGRAPH AND THE LIKE

(75) Inventors: Kensall D. Wise, Ann Arbor, MI (US); Richard Sacks, Ann Arbor, MI (US); Katharine T. Beach, Ann Arbor, MI (US); Joseph A. Potkay, Bay Village, OH (US); Masoud Agah, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 10/437,101

(22) Filed: May 13, 2003

(65) Prior Publication Data

US 2003/0233862 A1 Dec. 25, 2003

Related U.S. Application Data

(60) Provisional application No. 60/380,229, filed on May 13, 2002.

(51) Int. Cl.[7] ........................... H05B 3/00; G01N 30/02
(52) U.S. Cl. ....................... 219/209; 219/201; 73/23.39
(58) Field of Search ................................ 392/479, 480, 392/481, 482, 485; 219/209, 201, 476; 73/23.39

(56) References Cited

U.S. PATENT DOCUMENTS

| | | | |
|---|---|---|---|
| 4,881,410 A | | 11/1989 | Wise et al. |
| 4,966,037 A | * | 10/1990 | Sumner et al. ........... 73/204.26 |
| 5,025,346 A | * | 6/1991 | Tang et al. ............... 361/283.1 |
| 5,377,524 A | | 1/1995 | Wise et al. |
| 5,544,276 A | | 8/1996 | Loux et al. |
| 5,583,281 A | | 12/1996 | Yu |
| 5,792,943 A | * | 8/1998 | Craig ......................... 73/61.52 |
| 5,796,152 A | * | 8/1998 | Carr et al. .................. 257/415 |
| 5,955,932 A | * | 9/1999 | Nguyen et al. ............. 333/186 |
| 5,989,445 A | | 11/1999 | Wise et al. |
| 5,992,769 A | | 11/1999 | Wise et al. |
| 6,068,684 A | * | 5/2000 | Overton ....................... 96/104 |
| 6,068,780 A | | 5/2000 | Yu |
| 6,091,050 A | * | 7/2000 | Carr ........................... 219/201 |
| 6,096,656 A | | 8/2000 | Matzke et al. |
| 6,109,113 A | | 8/2000 | Chavan et al. |
| 6,134,944 A | | 10/2000 | Yu et al. |
| 6,184,504 B1 | * | 2/2001 | Cardella ..................... 219/513 |
| 6,193,501 B1 | * | 2/2001 | Masel et al. ................. 431/170 |
| 6,270,641 B1 | | 8/2001 | Griffiths et al. |
| 6,288,371 B1 | * | 9/2001 | Hamilton et al. ........... 219/530 |
| 6,386,014 B1 | | 5/2002 | Butch |
| 6,527,835 B1 | | 3/2003 | Manginell |
| 6,527,890 B1 | * | 3/2003 | Huang et al. ............. 156/89.11 |
| 6,537,437 B1 | | 3/2003 | Galambos et al. |
| 6,612,153 B2 | * | 9/2003 | White et al. ................ 73/23.42 |

* cited by examiner

*Primary Examiner*—Michael Cygan
(74) *Attorney, Agent, or Firm*—Brooks Kushman, P.C.

(57) ABSTRACT

A high-sensitivity, separation microcolumn assembly for a microgas chromatograph and the like is provided. The assembly has an ultra-low mass complete with integrated heaters. The assembly uses multiple zones for temperature control, and microstructures that permit very rapid heating and cooling of the microcolumn.

19 Claims, 5 Drawing Sheets

SEPARATION MICROCOLUMN ASSEMBLY FOR A MICROGAS CHROMATOGRAPH AND THE LIKE

CROSS-REFERENCE TO RELATED APPLICATION

This application claims the benefit of U.S. provisional application Ser. No. 60/380,229, filed May 13, 2002 and entitled "Applications-MicroGC."

STATEMENT REGARDING FEDERALLY SPONSORED RESEARCH OR DEVELOPMENT

This invention was made with Government support under Contract No. 998 6866, awarded by NSF-ERC. The Government has certain rights in the invention.

BACKGROUND OF THE INVENTION

1. Field of the Invention

This invention relates to separation microcolumn assemblies for microgas chromatographs and the like.

2. Background Art

There are numerous challenging issues associated with the realization of a fast microGC ($\mu$GC) utilized as a "fieldable analytical instrument." "Fieldable analytical chemistry" is defined as "the practice of producing appropriate qualitative and/or quantitative information with analytical instruments that are operated at or near the sample collection location and which convert data to chemical information in a time frame that is consistent with near real-time application."

GC systems are chemical instruments by which the components of a gaseous mixture can be separated, identified, and the constituent concentrations qualified. FIG. 1 shows the schematic of a GC system in which a sample is vaporized and injected onto the head of the separation column 10, the heart of the system. The sample is transported through the column by the flow of an inert, gaseous mobile phase. The column itself is coated with a stationary phase that greatly influences the separation of the various gaseous species. The structure of the stationary phase affects the amount of time the compounds take to move through the column. That is, as various molecules pass through the column, the time spent adsorbed on the stationary phase (column wall) is a function of the gas type, stationary phase used, and temperature. As compounds emerge from the column, they pass over a detector 12. The compound and detector interact to generate a signal whose size corresponds to the amount of compound present in the sample. The signal can be recorded by a recorder 14. The delay of a sample in passing through the column identifies the species present.

Conventional GC systems tend to be large, fragile, and relatively expensive table-top instruments. MEMS technology promises the realization of a complete microGC system with much smaller size, reduced analysis time and greatly-increased portability compared to its traditional ancestors. Such systems should make gas chromatography a pervasive method for gas analysis, with applications in monitoring food freshness, industrial process control, and the environment. The prospect of a wristwatch-size microsystem capable of analyzing the air we breathe with part-per-billion sensitivity would have wide applicability in homeland security.

As mentioned above, the basic—and the heart—of a GC system is its separation column. There are numerous efforts around the world to miniaturize the separation column (along with the rest of the instrument) and reduce its power consumption, allowing rapid changes in the column temperature and decreasing the analysis time. Sandia National Laboratories has recently introduced a football-size "miniGC" that is considered the state-of-the-art today.

The following U.S. patent documents are related to the present invention: U.S. Pat. Nos. 6,527,835; 6,096,656; 6,527,890; 6,386,014; 6,270,641; 6,134,944; 6,068,780; 5,792,943; 5,583,281; 5,544,276; 4,881,410; 5,377,524; 5,989,445; 5,992,769; and 6,109,113.

SUMMARY OF THE INVENTION

An object of the present invention is to provide improved separation microcolumn assemblies for a microgas chromatograph and the like.

In carrying out the above object and other objects of the present invention, a separation microcolumn assembly comprising a plurality of connected sections is provided. Each of the sections includes a substrate having a plurality of closely-spaced, gas-flow microchannels etched therein. A cover is connected to the substrate to sealingly close the microchannels.

The substrate may be a wafer-based substrate.

The cover may be a glass wafer bonded to the substrate or may include a dielectric layer.

The dielectric layer may be a CVD film.

The assembly may further include a base layer formed on surfaces defining the microchannels to serve as a base for stationary phase deposition.

Still further in carrying out the above object and other objects of the present invention, an assembly is provided including an elongated device, and a first microstructure having high thermal conductivity for dividing the elongated device into temperature zones to thermally isolate the zones from each other.

The zones may be located on a single level, and may be stacked in multiple levels.

The first microstructure may be a rib, and the rib may be a semiconductor rib.

The assembly may further include a plurality of spaced, individually-controllable heaters distributed along a length of at least one of the zones.

The assembly may further include a second microstructure having high thermal conductivity and a microactuator for moving the second microstructure to a cooling position to cool one of the temperature zones in response to an electrical signal.

The microactuator may be an electrostatic microactuator.

The second microstructure may be a plate.

The assembly may further include a heater and a microactuator for moving the heater to a heating position to heat one of the temperature zones in response to an electrical signal.

The heater may be a plate.

Yet still further in carrying out the above object and other objects of the present invention, in a microgas chromatograph, a micromachined, separation microcolumn assembly to separate a gas sample flowing therethrough into separate compounds is provided. The assembly includes a plurality of connected sections. Each of the sections includes a substrate having a plurality of closely-spaced, gas flow microchannels etched therein. A cover is connected to the substrate to sealingly close the microchannels.

Still further in carrying out the above object and other objects of the present invention, in a microgas chromatograph, a micromachined, separation microcolumn assembly to separate a gas sample flowing therethrough into separate compounds is provided. The assembly includes a microcolumn, and a first microstructure having high thermal conductivity for dividing the microcolumn into temperature zones and to thermally isolate the zones from each other.

The above object and other objects, features, and advantages of the present invention are readily apparent from the following detailed description of the best mode for carrying out the invention when taken in connection with the accompanying drawings.

DETAILED DESCRIPTION OF THE PREFERRED EMBODIMENTS

As described hereinbelow, a number of innovative approaches to column miniaturization are introduced that significantly improve the operation of microGCs and indeed make the concept of a "$\mu$GC sensor" realistic.

Figure 1:
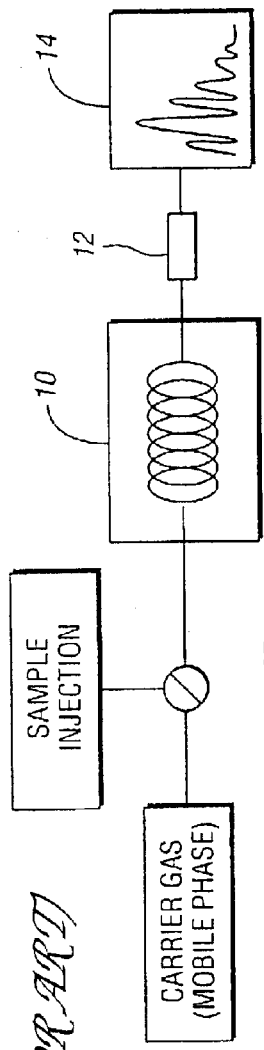
FIG. 1 is a schematic view of a prior art GC system.
Figure 2:
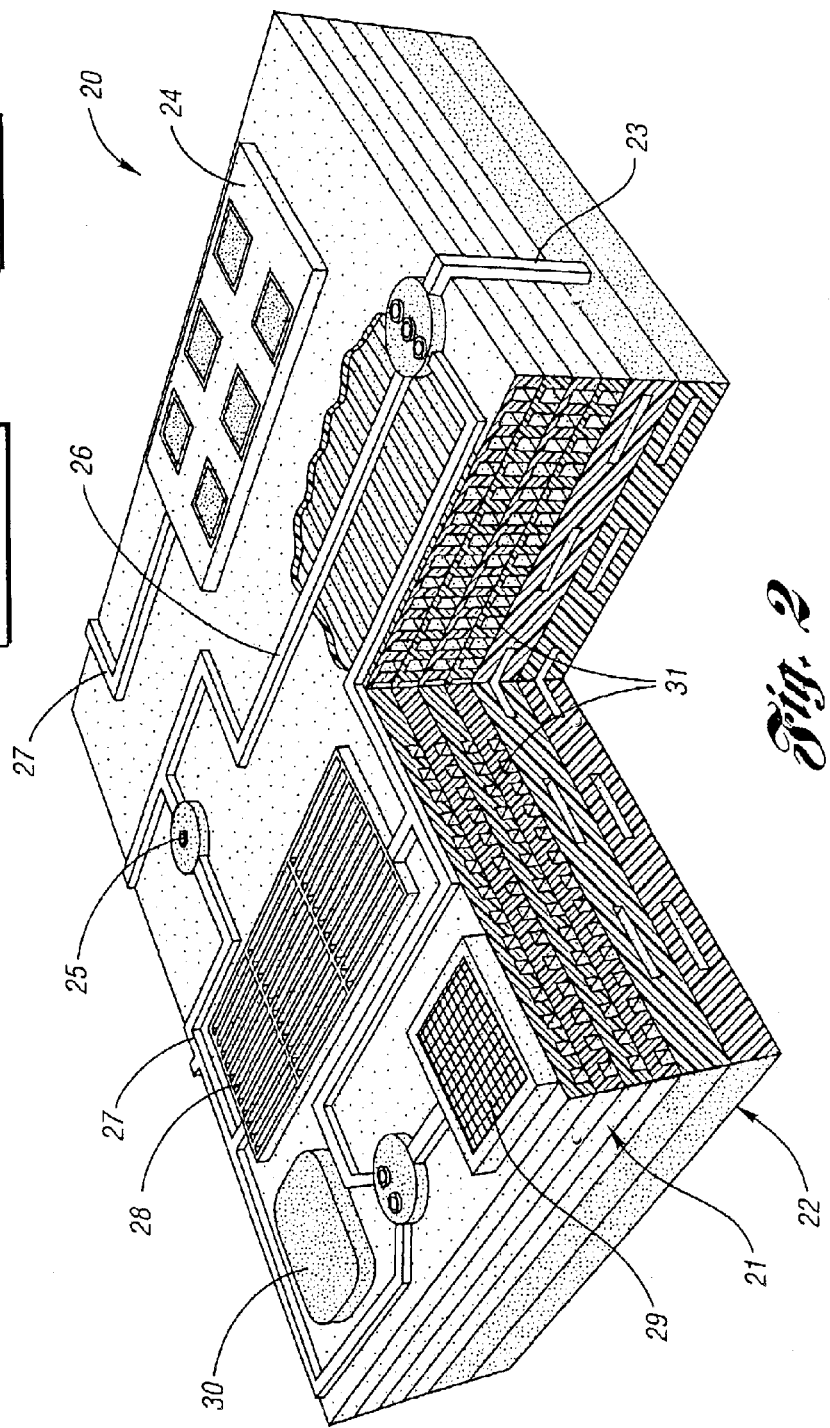
FIG. 2 is a perspective schematic view, partially broken away, of a MicroGas Chromatograph ($\mu$GC) constructed with a high-sensitivity, micromachined column assembly of the present invention.

A microgas chromatograph utilizing a micromachined separation microcolumn assembly of the present invention is generally indicated at 20 in FIG. 2. The assembly is generally indicated at 21 and is in the form of a stacked DRIE microcolumn.

The chromatograph also includes a distributed vacuum pump 22 having pump vias 23, a multi-sensor array 24, a latching bypass valve 25, sealed channel 26, column vias 27, a multi-stage pre-concentrator 28, a filtered inlet 29 and a calibration source 30. The assembly 21 also includes polar/non-polar columns 31.

Some of the proposed approaches are not only applicable to gas chromatography systems but also can be applied to other applications that require multi-zone temperature control and rapid temperature changes. It is noted in a GC, the column is typically heated to volatilize species of interest, with a temperatures up to 100° C. in common use. Minimizing the power associated with column temperature control is also described.

Microchannel fabrication using CVD is applicable to make channels with sensors and actuators that can be used in any microfluidic application where built-in transducers are needed and where heater/cooling elements are needed. A number of lab-on-a-chip embodiments would benefit from this.

The fast temperature response can be used in a number of lab-on-a-chip applications to enhance the reaction time. The fast heating and cooling can be used in IC applications where localized cooling or heating is used to improve performance of that IC stage at a lower cost than heating/cooling the entire chip. Energy only need be used to impact those portions of the chip that need it.

Microcolumn Function and Fabrication

Figure 3:
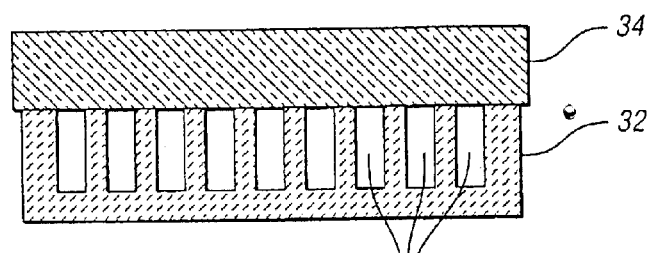
FIG. 3 is a side sectional schematic view of a microcolumn of the present invention.

The basic component of a microGC is the separation column. Two different techniques have been investigated to design and fabricate the microchannel. One method uses a deep high-aspect-ratio dry etching (DRIE) step to form the channel and an anodic bonding step to seal it, and the other employs a wet or dry etch to form the channel by undercutting a ceiling grid structure, followed by the use of a deposited (e.g., chemical-vapor-deposited (CVD)) film to close the channel. FIG. 3 shows that by using the DRIE process, narrow and closely spaced gas-flow channels 30 can be etched into a silicon (or other wafer-based) substrate 32. After etching the channel, the silicon substrate is thermally oxidized to produce a thin, glass-like layer on their surface. Deposited films could be used to coat the channel in addition to or in place of thermally-grown silicon dioxide. This coating serves as a base for stationary phase deposition. The channels are then sealed by anodic bonding the silicon wafer to a Pyrex wafer 34, typically Corning 7740, to close the channel. It should be noted that in order to reduce the mass of the DRIE channel, a deep boron diffusion can be used after the etch step so that after anodic bonding, the entire silicon-glass wafer sandwich can be placed in a suitable silicon etchant (EDP, KOH, hydrazine, TMAH) and the undoped portions of the silicon can be removed, retaining only the boron-doped silicon wall typically 2–16 $\mu$m in thickness, depending on the diffusion time and temperature.

When a column is formed in this way, pressure sensors can be integrated with the column using the method taught in U.S. Pat. Nos. 4,881,410 and 5,377,524 using a stub off of the channel to tap the pressure and running leads out of the sensor using methods such as that described in U.S. Pat. No. 6,109,113.

Figure 4:
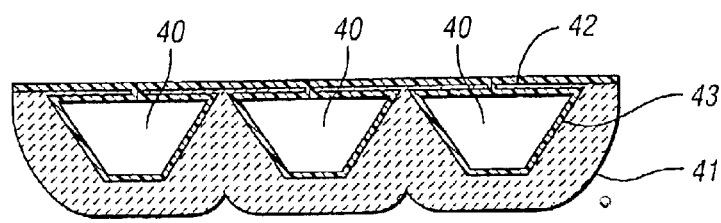
FIG. 4 is a side sectional view of another microcolumn of the present invention.

In the latter approach, which was originally developed for drug delivery and inkjet print head applications, as described in U.S. Pat. Nos. 5,989,445 and 5,992,769, microchannels indicated at 40 in FIG. 4 are being formed by wet/dry etching in a silicon substrate 41, undercutting a ceiling grid structure that can be formed from boron-doped silicon and/or a variety of grown or deposited dielectrics. When dry etching is used, either anisotropic or isotropic etching (or combinations thereof) can be used in order to obtain a wide variety of channel profiles. The channels 40 are then sealed by deposited dielectrics 42 (preferably, but not restricted to, chemical vapor-deposited films), as shown in FIG. 4. A coating 43 coats the channels 40 to serve as a base for stationary phase deposition.

This technique, which is proposed for GC column formation for the first time in this application, has some significant advantages when compared with other methods for column formation. It involves no anodic bonding, which inherently increases the yield. In addition, by eliminating the glass plate or lid of FIG. 3, it greatly reduces the thermal mass of the structure, resulting in a much faster response time. Since adding a front-back masking step is easy to retain a thick chip rim, pressure sensors, temperature sensors, heaters, and appropriate interface circuitry can be readily realized there. While the channel itself could be realized using a variety of discrete tubing, it is the ability to integrate a variety of temperature sensors, heaters, and pressure sensors on the column itself using this process that makes it especially attractive. It is noted that when a pressure sensor is needed on the column itself (not on the rim), it could be realized using surface micromachining techniques or with combination surface- and bulk-micromachined microstructures.

Figure 5:
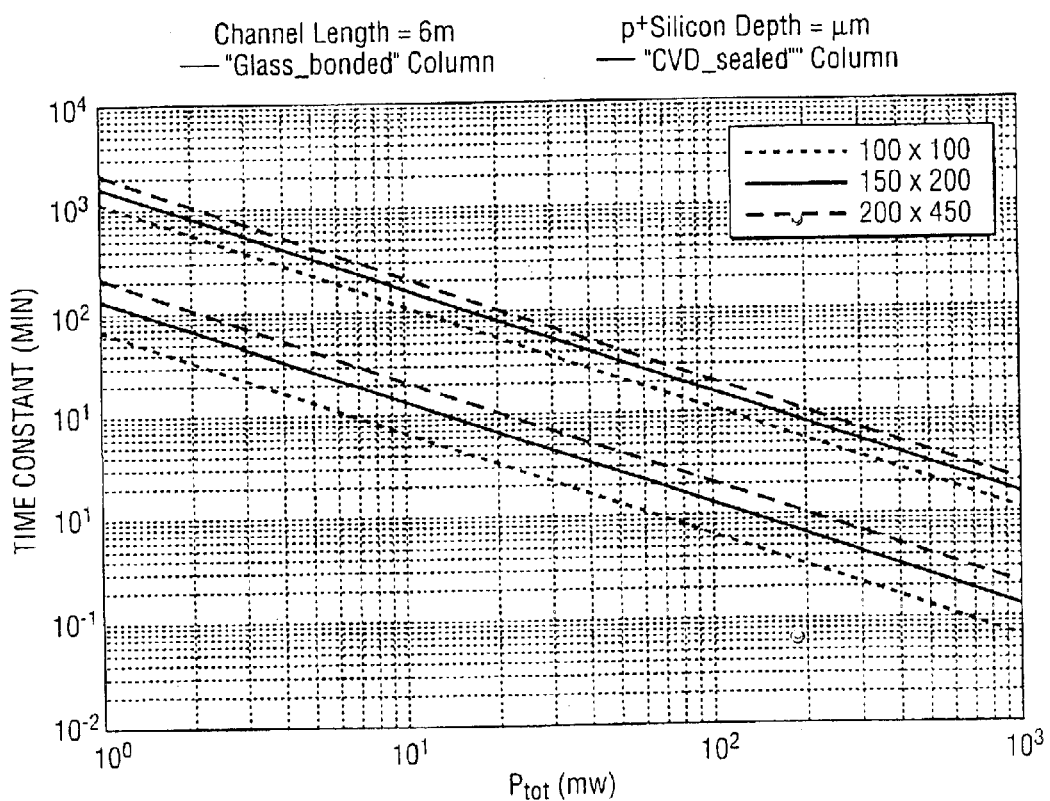
FIG. 5 shows graphs of thermal time constants of two column types for three different power consumptions.

FIG. 5 shows the thermal time constants of the two structures for three different cross-sectional areas. As can be seen, if the two structures have identical channel dimensions of 150 $\mu$m (wide)×250 $\mu$m (deep)×6 m (long) and are designed to achieve a temperature rise of 100° C. at 10 mW of operating power, the glass-bonded channel shows a time constant of 154 min whereas the corresponding value for the CVD-sealed column is 12.5 min. Moreover, to achieve a temperature rise of 100° C. in 200 sec, the anodically-bonded column needs a transient power spike of about 450 mW while the CVD column needs only 45 mW; consequently, the battery requirements are much stricter (and perhaps prohibitive) for the glass-bonded column. These results make the CVD-sealed columns a more promising choice for the realization of a low-power, battery-operated, temperature-programmed fast $\mu$GC. It is also noteworthy that regardless of the column type, the column entry sections (inlet and outlet), which are inherently part of the silicon channel, must be converted to silicon dioxide (or other suitable thermal insulator) for an operating power lower than 100 mW. This, itself, is a challenging issue in column fabrication.

Multi-Zone Temperature Control

In some applications, such as gas chromatography, it is an advantage to divide the device into different zones and control the temperature of each zone independently. In a GC system, this ability is likely to allow more effective separation than would the normal microchannel. Using the different thermal desorption profiles of different gaseous species, the temperature of different column sections could be controlled to speed or delay particular species, thus enhancing separation of a target molecules. Although temperature-programmed desorption is a commonly-used technique in macro-GCs, the use of multiple zones (two to dozens or even hundreds) is thought to be new and the ways for implementing such structures are thought to be novel.

Figure 6:
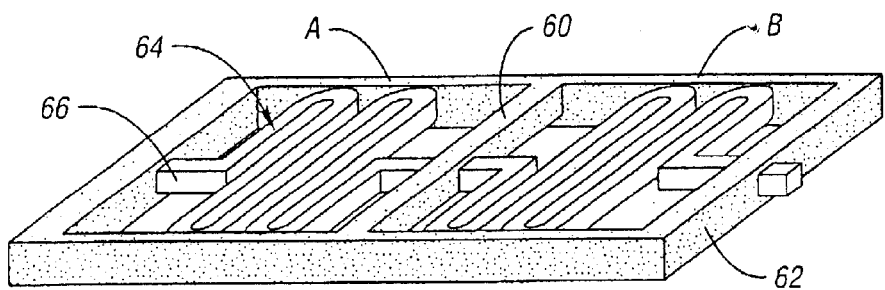
FIG. 6 is a perspective schematic view of a microcolumn surrounded by a silicon rim with temperature zones A and B isolated by a silicon rib.

To realize the idea of multi-zone temperature control, different zones should be isolated from each other. Silicon, thanks to its high thermal conductivity, has the potential to decrease the loading effect of individual zones on each other significantly, providing a high level of inter-zone isolation. FIG. 6 shows how a silicon rib 60 can be employed to create a short thermal circuit to the ambient at the interface between two adjacent temperature zones, A and B. Also shown in FIG. 6 is a silicon rim 62 surrounding a microcolumn 64 which has a gas entry 66. This method provides the opportunity to program and control the temperature of each zone separately. Zones can be formed on one level, as shown in FIG. 6, or on different stacked layers.

As noted above, traditional GCs use temperature programming to decrease the analysis time. The dependence of GC retention on vapor pressure means that mixtures containing components with a wide range of boiling points cannot be separated satisfactorily in an isothermal run. The more volatile components may be well enough resolved, but the higher boiling materials will only be eluted with long retention times and very broad peaks. If the column temperature is high enough to give satisfactory peaks for the less volatile compounds, the low-boiling constituents will be less resolved. The solution is to raise the column temperature (either continuously or in steps) during a chromatographic run, so that for a homologous series peaks emerge at regular intervals. This is called "temperature programming." The multi-zone temperature control adds this ability to do temperature programming at different zones independently, which is likely to improve the GC operation significantly. In that case, it will open a new era in fast gas chromatography.

Either in an isothermal run, i.e. constant temperature, or during temperature-programmed operation, the column temperature should be controlled to within about a tenth of a degree for a precise work since the partitioning behavior is quite dependent on temperature. To reach this goal, different temperature sensors will be placed along the channel length at each zone to provide the required information as feedback for a closed-loop controller. Additional desirable characteristics of the chromatograph system are low thermal mass for fast cool-down at the conclusion of the analysis and rapid temperature response to follow accurately the temperature program profile. Some solutions to achieve these characteristics have already been addressed and the rest will be discussed in the following section.

Figure 7:
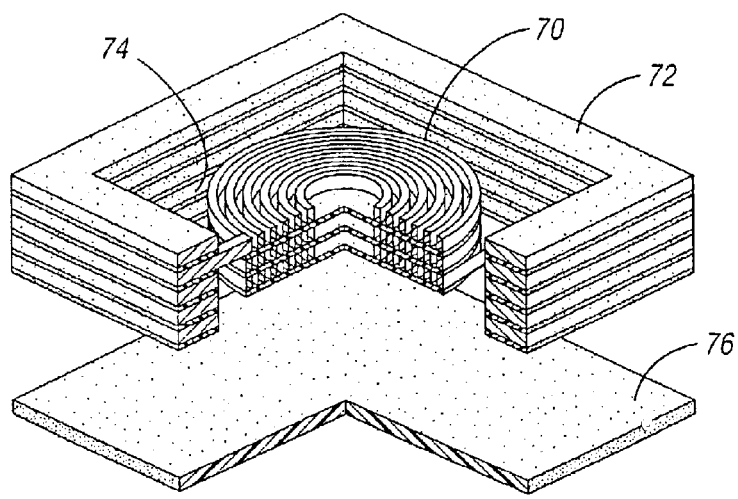
FIG. 7 is a perspective schematic view, partially broken away, of a $\mu$GC column of the present invention.

In order to frame the discussion of the $\mu$GC column, FIG. 7 shows one possible view of a stacked column arrangement wherein a heated column 70 is suspended from a stacked sealing rim structure 72 within a vacuum cavity 74. A sealing cap 76 is also provided.

This could be realized by a stack of silicon-glass substrates, as in the DRIE approach noted above, or it could be obtained using the CVD-sealed approach, in which case the interleaving dielectric layer would be a thin film. In either case, the structure would be vacuum sealed to minimize heat losses from the column and thermally isolate it as much as possible. Thus, the shell around the device, consisting of the wafer rims, would remain at ambient while the column was suspended in vacuum by the entry and exit lengths of the column.

Fast Temperature Response

One of the major issues in designing a low-power fast microGC is the speed of temperature changes. To minimize power consumption, the thermal resistance between the structure and the ambient should be very large. Moreover, due to the long channel used in GC applications, the structure tends to have a high mass, and hence the thermal capacitance is large. As a result, the thermal response time is very large, both in heating-up and in cooling-down. For instance, as shown in FIG. 5, the response time exceeds one hour for a channel with the dimensions of 150 $\mu$m×250 $\mu$m×6 m. Here, two solutions are introduced, which address the heating and cooling response times separately.

Figure 8A:
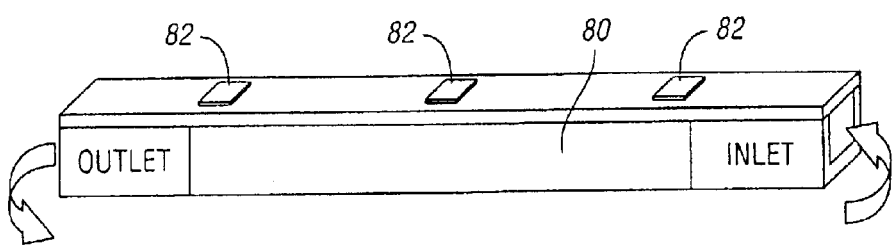
FIGS. 8a and 8b are perspective schematic and thermal equivalent half-circuit views, respectively, of a simple channel of the present invention.

To increase the temperature of the channel, two heaters are located at the inlet and outlet ports of each zone, as shown in FIG. 8a. These heaters compensate any heat loss through the interface of the channel with the outside world via the entry and exit lengths. By using a feedback controller, it is possible to increase the heating speed with a power spike for a short period of time if the battery is able to drive it. However, this does not provide a uniform temperature increase across the channel. In fact, during the transient the temperature difference across the different parts of the channel at each zone can be high.

Figure 8B:
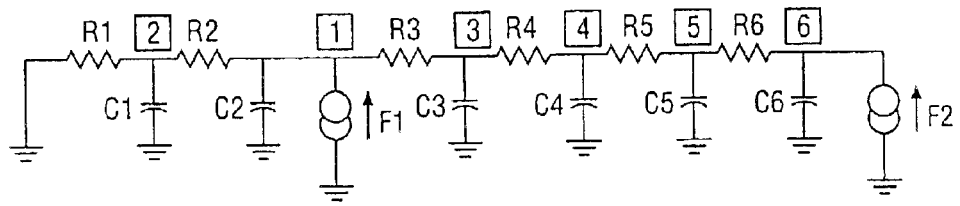
Figure 9A:
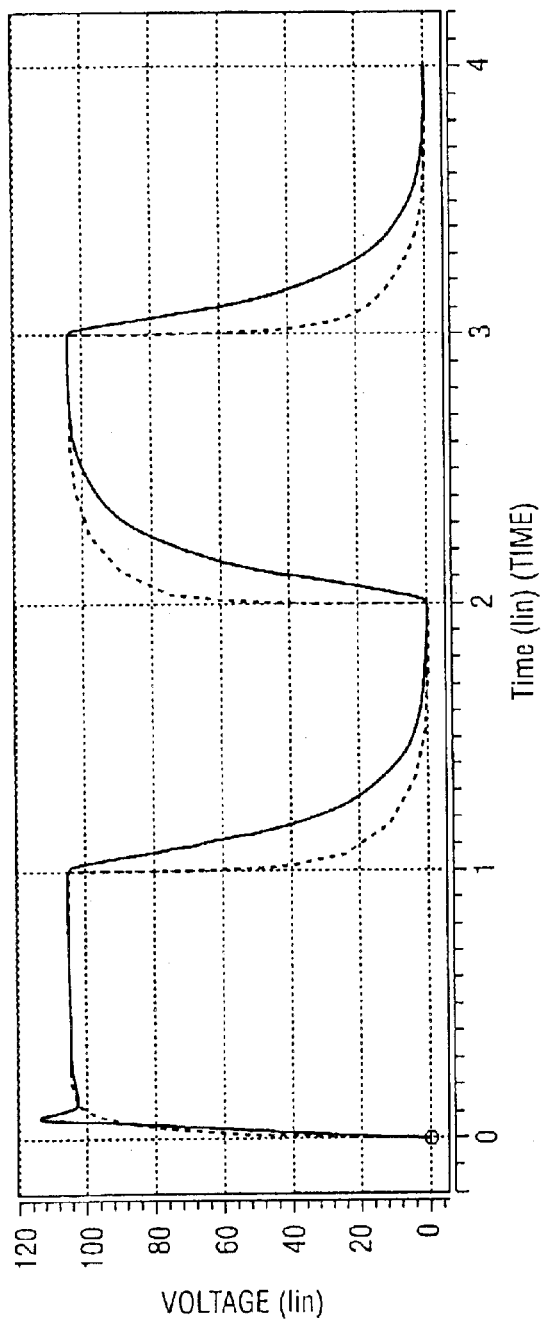
FIGS. 9a and 9b are graphs of voltages and currents, respectively, versus time when a middle heater is employed for a short period of time which reduces the heating response time and the associated temperature gradient; the cool-down time remains unaffected.
Figure 9B:
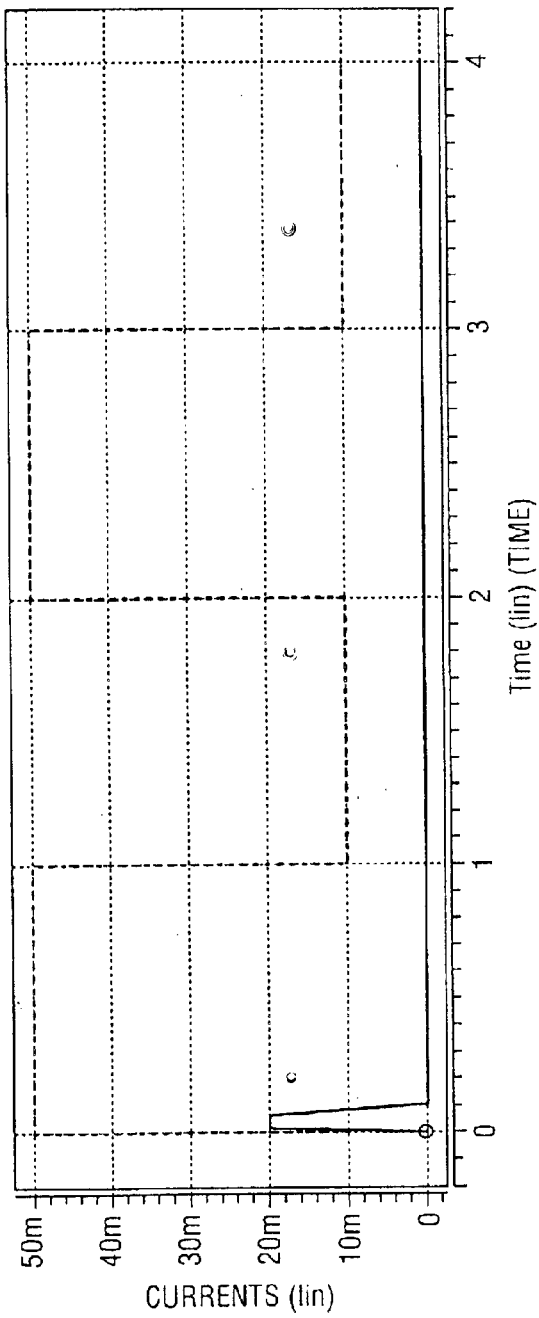

To overcome this difficulty, the use of distributed heaters is recommended to lower the response time and achieve a uniform temperature during the heating process. This approach does not change the static power consumption but increases the complexity of the controller. To see how this tactic works, consider the simple structure of FIG. 8a. It shows a 5 mm long channel 80 with three heaters 82. Two heaters are located at the input and output ports of the channel and one heater is placed in the middle. F1 and F2 in the circuit of FIG. 8b represent the power of the entry heater and the middle heater, respectively. The middle heater is turned on only in a short period of time to improve the heating process. Simulation results are shown in FIGS. 9a and 9b. As can be seen, in this short channel the response time is about 1 s, which can be reduced significantly if the middle heater is turned on for only 20 ms. Additionally, the temperature difference between the entry of the channel and the middle is diminished.

In any case the cool-down speed is low because when the heaters are off, the heat dissipates only through input and output ports, which have a very high thermal resistance. As mentioned before, this time can go beyond one hour for a 6 m long channel with 150 $\mu$m×250 $\mu$m cross sectional area. Some means must be found for reducing it.

Figure 10A:
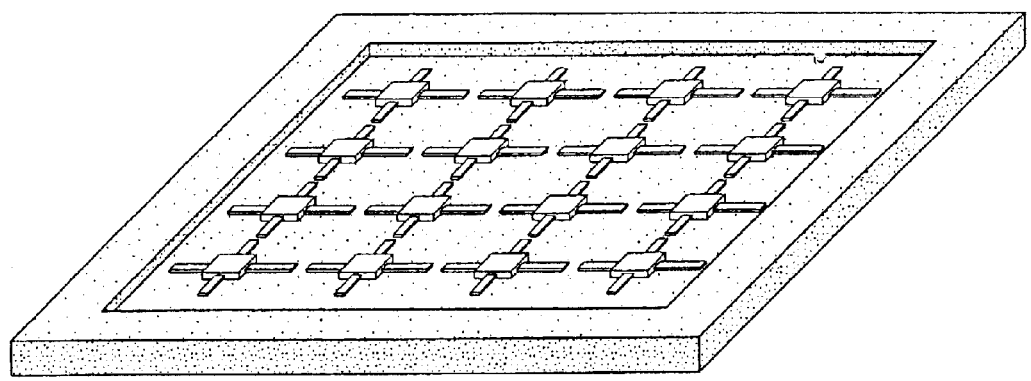
FIGS. 10a and 10b are perspective schematic views of an array of movable microstructures that can be moved upward to contact the column, providing a programmable thermal resistance to ambient; they are shown at rest in FIG. 10a and activated in FIG. 10b; in vacuum, they provide a large decrease in thermal resistance when contact is made.

For cool-down, a solution is to reduce the thermal resistivity to ambient during cool-down. It can be achieved by increasing the number of paths for heat dissipation. The method is to employ another structure consisting of an array of individual movable plates, i.e. microactuators. FIG. 10a shows a schematic of such a device at its rest position. This structure is placed either above or below the channel at a precisely controlled distance. It should be noted that the microactuator type is not an issue as long as it operates at low power and provides a low-thermal-resistance path. Electrostatic actuators are good candidates because they meet the above requirements. This approach is especially effective for a vacuum-sealed column such as that shown in FIG. 7 since convective and conductive paths are normally absent, even across a very narrow gap. Thus, by moving the plates up only a few microns or less, a very large difference in thermal loading can be achieved.

Figure 10B:
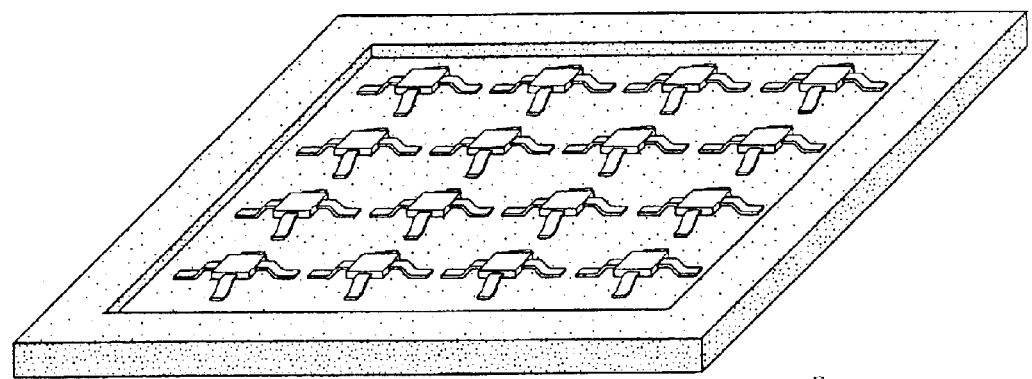

The actuators will operate in a normally-open condition and will be activated only during cool-down. When set in motion, these movable plates will be elevated as shown in FIG. 10b. The actuators can be formed from silicon plates suspended by straight, corrugated, or crab-leg struts, among others. The motion will be small, but in the range from 1–20 $\mu$m or more, depending on the actuation and support. For electrostatic actuation, an area separated from the column (the opposing plate) by no more than a few microns is necessary to ensure a low actuation voltage. This could be a sub-area of the total plate if a rolling suspension is used. The number of elevated microactuators along with the contact time dictates the cool-down speed. The more contact time and the greater the number of active plates, the less the cool-down response time. This provides the opportunity to tune and program the cool-down speed. If the array itself is divided into different zones, corresponding to the microcolumn temperature zones, then the cool-down profile can be programmed for each zone separately.

Figure 11:
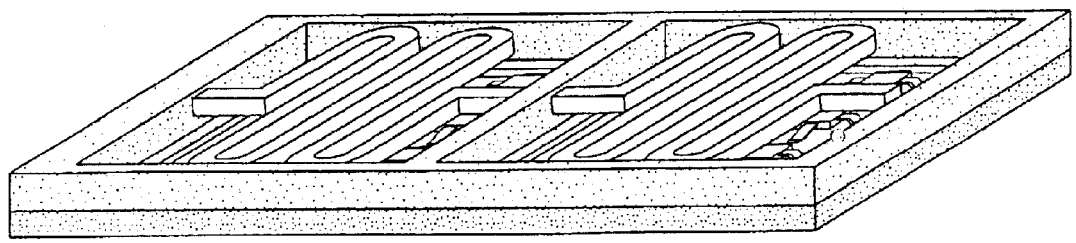
FIG. 11 is a perspective schematic view of a micro separation column of the present invention coupled to a cool-down mechanism.

Realization of this approach also suggests a new technique for increasing the heating speed. If one set of plates is heated (electrostatically actuated or thermally actuated) and a second set consists of plates at ambient temperature, then the first type can be moved up to heat the column and the second moved up to cool it. Fast heating and cooling should result. FIG. 11 shows the column overlayed on the plate array as it would be in operation.

The combination of multi-zone temperature control, very low mass and high heating efficiency, and rapid cooling/heating times make a microGC a powerful fieldable analytical instrument. A microcontroller measures the temperature of each individual zone using multiple temperature sensors and then adjusts power to the heaters to achieve the desired zone temperature and temperature-programming rate. Multi-zone control provides the opportunity to reduce separation time and increase the channel efficiency. Using distributed heaters at each zone guarantees a rapid and uniform heating process. Also, for rapid cooling-down of the column at each zone, the movable plates within that zone are elevated to touch the device and provide supplementary paths for the heat dissipation. The microcontroller sets the time of actuation and the number of in-contact actuators as a tool to program the speed of temperature decrease. This approach of using contacting plates on the micro-scale to adjust the cooling (and heating) time could be used in a variety of structures beyond the $\mu$GC wherever thermal responses are important.

The following are features of the invention which are believed to be novel:

1) The use of CVD-sealed microchannels to achieve very low mass for rapid thermal cycling and high separation in gas analysis. Possibly this could include etching techniques such as the use of a deep dry etch through a ceiling grid for high aspect ratios followed by a short wet isotropic or anisotropic lateral etch to form the channel, or the use of a uniform isotropic dry etch through a dielectric/silicon ceiling to form circular channels, whose shape can be modulated based on etch properties.

2) The use of multiple temperature zones in an integrated column to enhance separation capabilities, with precise control over the temperature profile of each zone.

3) The use of movable microstructures to control the thermal access resistance to temperature-controlled elements such as GC column sections, along with possible implementations using the dissolved-wafer process or surface micromachining.

The $\mu$GC itself can be applied to most applications where traditional GC's are used. The advantage will be faster response and lower cost for the apparatus. A unique advantage of the $\mu$GC is that it can be made portable and taken to sites where rapid analysis is required. This will make the $\mu$GC especially valuable for safety and security applications, including analysis at remediation sites.

The fabrication processes for the $\mu$GC will have commercial values beyond that. The micro channel fabrication using CVD is applicable to make channels with sensors and actuators that can be used in any microfluidic application where built-in transducers and heater/cooling elements are needed. A number of lab-on-a-chip embodiments would benefit from this technology.

The fast temperature response can be used in a number of lab-on-a-chip applications to enhance the reaction time. The fast heating and cooling can be used in IC applications as well where localized cooling or heating is used to improve performance of that IC stage at a lower cost than heating/cooling the entire chip. Energy is only required to be used to impact those portions of the chip that need it.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. An assembly comprising:
    a sealed structure having a vacuum cavity;
    a vacuum sealed microcolumn suspended from the structure in the vacuum cavity wherein heat losses from the device are minimized and the device is thermally isolated; and
    a first microstructure having high thermal conductivity for dividing the elongated device into temperature zones and to thermally isolate the zones from each other.

2. The assembly as claimed in claim 1, wherein the zones are located on a single level.

3. The assembly as claimed in claim 1, wherein the zones are stacked in multiple levels.

4. The assembly as claimed in claim 1, wherein the first microstructure is a rib.

5. The assembly as claimed in claim 4, wherein the rib is a semiconductor rib.

6. The assembly as claimed in claim 1, further comprising a plurality of spaced, individually-controllable heaters distributed along a length of at least one of the zones.

7. The assembly as claimed in claim 1, wherein the structure includes a rim structure.

8. The assembly as claimed in claim 7, wherein the microstructure creates a short thermal circuit to the rim structure.

9. The assembly as claimed in claim 1, wherein the microcolumn is suspended in the vacuum cavity at entry and exit portions of the microcolumn.

10. An assembly comprising:
    a sealed structure having a vacuum cavity;
    a elongated device suspended from the structure in the vacuum cavity wherein heat losses from the device are minimized and the device is thermally isolated;
    a first microstructure having high thermal conductivity for dividing the elongated device into temperature zones and to thermally isolate the zones from each other; and
    a second microstructure having high thermal conductivity and a microactuator for moving the second microstructure to a cooling position to cool one of the temperature zones in response to an electrical signal.

11. The assembly as claimed in claim 10, wherein the microactuator is an electrostatic microactuator.

12. The assembly as claimed in claim 11, wherein the second microstructure is a plate.

13. The assembly as claimed in claim 10, further comprising a heater and a microactuator for moving the heater to a heating position to heat one of the temperature zones in response to an electrical signal.

14. The assembly as claimed in claim 13, wherein the heater is a plate.

15. An assembly comprising:
    a sealed structure having a vacuum cavity;
    a elongated device suspended from the structure in the vacuum cavity wherein heat losses from the device are minimized and the device is thermally isolated;
    a first microstructure having high thermal conductivity for dividing the elongated device into temperature zones and to thermally isolate the zones from each other; and
    a heater and a microactuator for moving the heater to a heating position to heat one of the temperature zones in response to an electrical signal.

16. The assembly as claimed in claim 15, wherein the heater is a plate.

17. An assembly comprising:
    a sealed structure having a vacuum cavity;
    a elongated device suspended from the structure in the vacuum cavity wherein heat losses from the device are minimized and the device is thermally isolated; and
    a first microstructure having high thermal conductivity for dividing the elongated device into temperature zones and to thermally isolate the zones from each other wherein the structure includes a rim structure.

18. The assembly as claimed in claim 17, wherein the first microstructure creates a short terminal circuit to the rim structure.

19. An assembly comprising:
    a sealed structure having a vacuum cavity;
    a elongated device suspended from the structure in the vacuum cavity wherein heat losses from the device are minimized and the device is thermally isolated; and
    a first microstructure having high thermal conductivity for dividing the elongated device into temperature zones and to thermally isolate the zones from each other wherein the device is suspended in the vacuum cavity at entry and exit portions of the device.

* * * * *